United States Patent [19]

Braden

[11] Patent Number: 4,872,786
[45] Date of Patent: Oct. 10, 1989

[54] SOLID PARTICULATE AEROSOL GENERATOR

[76] Inventor: Thomas M. Braden, 5737-G Arrow Hwy., Montclair, Calif. 91763

[21] Appl. No.: 34,914

[22] Filed: Apr. 6, 1987

[51] Int. Cl.$^4$ .................... B65G 53/46; B65G 53/08
[52] U.S. Cl. ......................... 406/68; 406/63;
406/136; 55/97; 55/270
[58] Field of Search .................. 406/62–68,
406/93, 127, 128, 136, 137, 151, 153, 197;
222/636; 55/97, 270

[56] References Cited

U.S. PATENT DOCUMENTS

| | | | |
|---|---|---|---|
| Re. 31,952 | 7/1985 | Wilcox et al. | 55/270 X |
| 2,011,133 | 8/1935 | Yoss | 406/63 X |
| 3,152,733 | 10/1964 | Ross | 406/62 |
| 4,055,075 | 10/1977 | Allan et al. | 55/270 X |
| 4,213,768 | 7/1980 | Bauman et al. | 55/97 |
| 4,324,568 | 4/1982 | Wilcox et al. | 55/97 |

FOREIGN PATENT DOCUMENTS

| | | | |
|---|---|---|---|
| 816590 | 7/1969 | Canada | 406/63 |
| 707791 | 7/1941 | Fed. Rep. of Germany | 406/63 |

OTHER PUBLICATIONS

Product Data Sheet for "Unifab Particulate Generator", published by Unifab Corporation of Kalamazu, Mich.–Publishing date unknown.

Primary Examiner—Joseph F. Peters, Jr.
Assistant Examiner—James M. Kannofsky
Attorney, Agent, or Firm—Sheldon & Mak

[57] ABSTRACT

An apparatus and a method are provided for producing a solid particulate aerosol which is sufficiently precise in concentration to be suitable for testing HEPA filters. The apparatus continuously delivers a measured quantity of a solid particulate material to a mixer where it is combined with a controlled flow of gas. The solid particulate material is delivered to the mixer in precisely measured quantities via pockets of constant volume which are disposed radially and equidistantly about a rotating wheel.

11 Claims, 3 Drawing Sheets

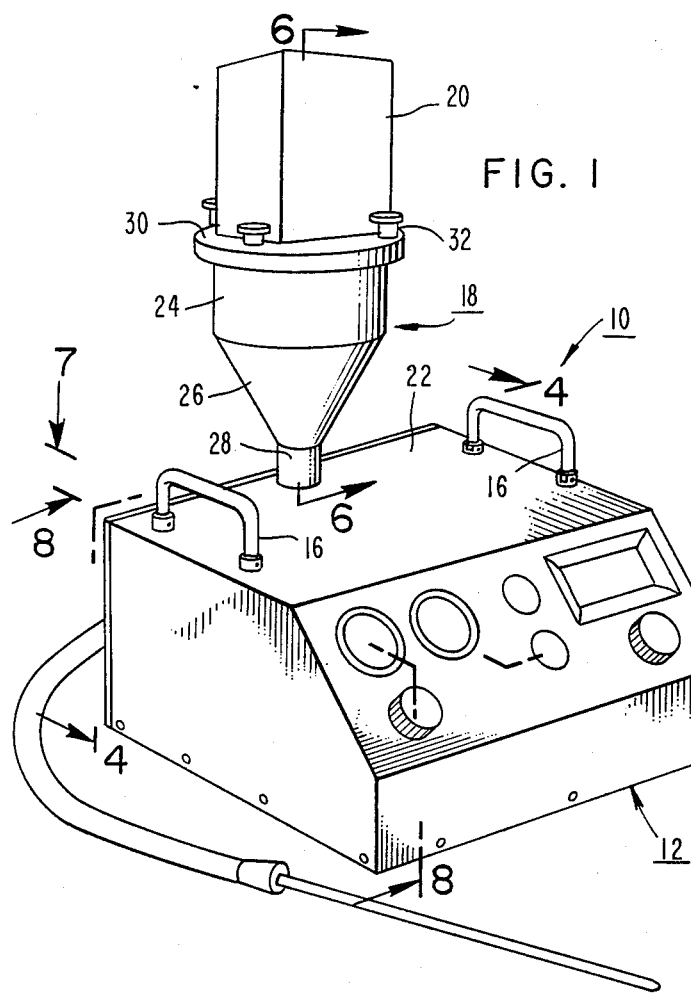
FIG. 1
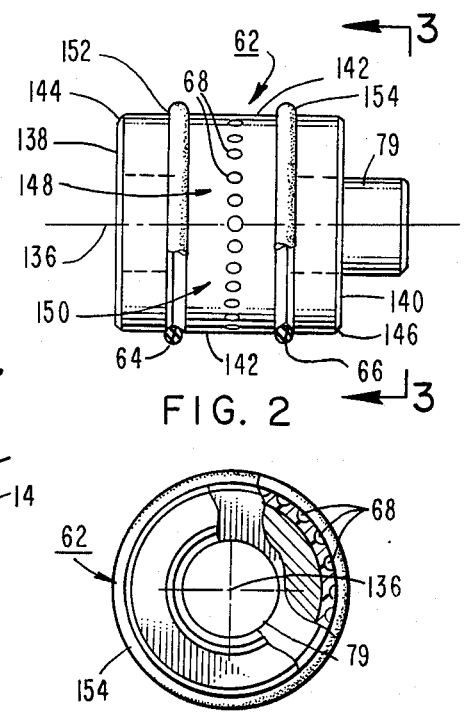
FIG. 2
FIG. 3
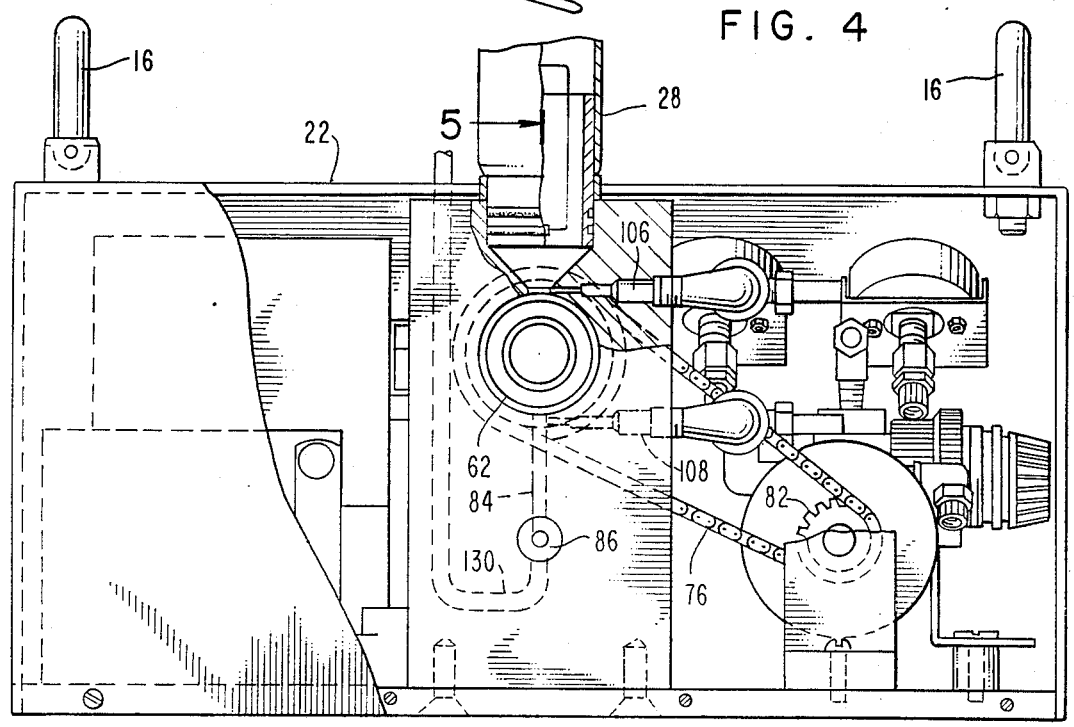
FIG. 4

SOLID PARTICULATE AEROSOL GENERATOR

BACKGROUND

The present invention is generally directed to a device for generating a solid particulate aerosol, and particularly to such a device capable of accurately dispensing a predetermined quantity of a solid particulate material within a unit quantity of a gaseous material.

It is desirable in many industrial applications to generate a solid particulate aerosol. Examples where such aerosols are desirable include the powder painting industry where metallic objects are electrically charged and then exposed to a solid particulate aerosol consisting of oppositely charged pigment particles. The pigment particles are electrically attracted to the charged metallic objects, thereby coating such objects with a uniform pigment layer.

Conventional solid particulate aerosol generators, such as those presently used in the powder painting industry, comprise a carrier gas which is caused to flow through a venturi, the throat of which venturi is in fluid communication with a particulate reservoir. As the carrier gas passes through the venturi, particulate matter from the reservoir is drawn by vacuum into the throat of the venturi where it is mixed with the carrier gas. However, conventional particulate aerosol generators of the type described above do not work well where the particulate matter is relatively small (mean average diameter less than about 0.2 microns) because small particles tend to form irregular clumps which, when dispersed by conventional generators, form aerosols having widely fluctuating particle concentrations. Conventional solid particulate aerosol generators also do not work well where the particle concentration of the aerosol needs to be maintained with high precision. Conventional aerosol generator are simply not capable of high precision.

An additional drawback to convention solid particulate aerosol generators is that such generators are not particularly flexible in that they tend to produce a very limited range of particle concentrations. Increasing the volume of carrier gas through the venturi tends to increase the vacuum formed in the venturi throat which, in turn, tends to increase the quantity of solids drawn into the carrier gas stream.

A specific area where conventional solids particulate aerosol generators are especially deficient is in the testing of high efficiency particulate air filters (HEPA filters), such as the filters used in hospitals, clean rooms and electronic assembly areas. The testing of HEPA filters using a solid particulate aerosol is described in U.S. Pat. No. 4,213,768, which patent is incorporated by reference herein as if fully set forth in its entirety. As described in U.S. Pat. No. 4,213,768, HEPA filters must be frequently tested to assure their continued efficiency. Testing with a solid particulate aerosol has marked advantages over testing with liquid aerosols, but the testing of these ultra-efficient filters with a solid particulate aerosol requires exposing the filters to an aerosol having a very specific concentration of ultra-fine particles (generally such particles must be less than about 0.2 microns). Conventional solids particulate aerosol generators are incapable of producing such a specifically concentrated aerosol. The ultra-fine nature of the test particles cannot be accurately metered into the carrier gas. The resulting aerosols have concentrations which fluctuate over a wide range, making any calculation of the filter's efficiency impossible.

There is therefore a need for a solid particulate aerosol generator which can accurately disperse particles having a mean average diameter smaller than about 0.2 microns.

There is a further need for a solid particulate aerosol generator which can produce aerosols with a highly precise concentration of solids material.

There is a still further need for a solid particulate aerosol generator which can adjustably produce aerosols having a wide variety of solids concentrations.

There is a still further need for a solid particulate aerosol generator which can produce a highly specific concentration of ultra-fine particles so as to be useful in the testing of HEPA filters.

SUMMARY

The solid particulate aerosol generator of the invention satisfies these needs. The invention provides a solid particulate aerosol generator capable of producing a highly precise aerosol concentration of ultra-fine particles, having an average mean diameter less than about 0.2 microns. The solid particulate generator of the invention is ideally suited for providing solid aerosols for the testing of HEPA filters. Additionally, the solid particulate aerosol generator of the invention is highly flexible, being capable of providing a wide range of precise particle concentrations by the mere turning of a dial.

The invention provides a solid particulate aerosol generator and a method for its use. The solid particulate aerosol generator of the invention comprises a solid particulate aerosol generator for accurately dispersing a predetermined quantity of a solid particulate material having a mean diameter less than about 0.2 microns, so as to provide a highly precise aerosol concentration of the particulate material which is useful in the testing of HEPA filters, the solid particulate aerosol generator comprising:

(a) a reservoir for storing the solid particulate material;

(b) a wheel rotatable about a horizontal axis of rotation, the wheel being disposed below and in fluid communication with the reservoir, the wheel being a right circular cylinder having a first end surface, a second end surface and a continuous radial surface, the radial surface abutting the first end surface along a first radial edge and the radial surface abutting the second end surface along a second radial edge, the radial surface having an upper radial surface moiety above the axis of rotation and a lower radial surface moiety below the axis of rotation;

(c) a first o-ring groove disposed radially around the radial surface proximate to the first radial edge and a second o-ring groove disposed radially around the radial surface proximate to the second radial edge, the first o-ring groove and the second o-ring groove being disposed in parallel planes which are perpendicular to the axis of rotation;

(d) a first o-ring disposed within the first o-ring groove and a second o-ring disposed within the second o-ring groove;

(e) at least four pockets disposed evenly around the radial surface between the o-ring grooves, each pocket having a predetermined volume and a single open side;

(f) scraping means disposed proximate to the radial surface upper moiety for scraping excess solid particulate material from above the single open side of each pocket;

(g) a conveying conduit disposed below and in fluid communication with the radial surface lower moiety; and (h) a venturi mixer having a throat in fluid communication with the conveying conduit and having an inlet side and a delivery port.

The solids particulate aerosol generator of the invention is constructed so as to allow solid particulate material to be conveyed from the reservoir to the pocket, deposited in the pocket, and conveyed in pocket volume quantities at a predetermined rate to the gas conduit where it is evenly distributed within a predetermined flow of gas. The gas-particulate mixture is then propelled along the gas conduit to the gaseous atmosphere where it forms a solid particulate aerosol.

The invention also provides a method for producing a solid particulate aerosol comprised to particles having a mean diameter less than about 0.2 microns comprising the steps of:

(a) conveying solid particulate material from a reservoir to a rotating wheel wherein the wheel is rotatable about a horizontal axis of rotation, the wheel being disposed below and in fluid communication with the reservoir, the wheel being a right circular cylinder having:
  (i) a first end surface, a second end surface and a continuous radial surface, the radial surface abutting the first end surface along a first radial edge and the radial surface abutting the second end surface along a second radial edge, the radial surface having an upper radial surface moiety above the axis of rotation and a lower radial surface moiety below the axis of rotation;
  (ii) a first o-ring groove disposed radially around the radial surface proximate to the first radial edge and a second o-ring groove disposed radially around the radial surface proximate to the second radial edge, the first o-ring groove and the second o-ring groove being disposed in parallel planes which are perpendicular to the axis of rotation;
  (iii) a first o-ring disposed within the first o-ring groove and a second o-ring disposed within the second o-ring groove;
  (iv) at least four pockets disposed evenly around the radial surface between the o-ring grooves, each pocket having a predetermined volume and a single open side; the solid particulate material being conveyed to the wheel so that the solid particulate material is deposited into the pockets at a first location on the upper radial surface moiety;

(b) scraping the excess solid particulate matter from above the open side of each pocket;

(c) rotating the wheel to convey the pockets containing the solid particulate material from the first location to a second location on the lower radial surface moiety;

(d) conveying the solid particulate material from the pockets at the second pocket location to a conduit wherein is flowing a gas;

(e) distributing the solid particulate material into the flowing gas to form a gas-solid mixture; and (f) discharging the gas-solid mixture into the atmosphere.

The invention also provides a method for testing a HEPA filter comprising the steps of (i) exposing the HEPA filter to a solid particulate aerosol produced by the method described in the preceding paragraph; and (ii) measuring the quantity of particles passing through the HEPA filter from the solid particulate aerosol to the atmosphere on the opposite side of the HEPA filter.

In one embodiment of the invention, solid particulate material is stored in a hopper from which it is conveyed by gravity to the top of a positive displacement wheel comprising a continuous row of pockets (depressions) of equal volumes disposed radially about the wheel. The solid particulate material from the hopper is deposited into each of the pockets as the wheel is rotated. The rotation of the wheel then rotates the pocket towards the bottom side of the wheel. The excess material is scraped off with a knife edge so that the quantity of material in each pocket is always the same. As each pocket is rotated to the underside of the wheel, the particulate material gravitates out of each conduit attached orthagonal to the throat of a venturi. Flowing through the venturi is a metered quantity of a carrier gas, such as air, from a carrier gas source, such as a compressed gas cylinder or a compressor. The flow of the carrier gas through the venturi draws the particulate matter into the venturi throat where it is mixed with the carrier gas. The carrier gas-particulate material mixture is thereafter discharged from the end of the venturi to form a precisely concentrated solids particulate aerosol.

DRAWINGS

These and other features, aspects and advantages of the present invention will become better understood with reference to the following description, appended claims and accompanying drawings where:

FIG. 1 is a perspective view of a solid particulate aerosol generator embodying features of the invention;

FIG. 2 is a side view of an indented wheel useful in the embodiment of the solid particulate aerosol generator of the invention shown in FIG. 1;

FIG. 3 is a partial cross-sectional view of the wheel shown in FIG. 2;

FIG. 4 is partial cross-sectional view of the solid particular aerosol generator of FIG. 1 taken along plane 4—4;

DESCRIPTION

Figure 5:
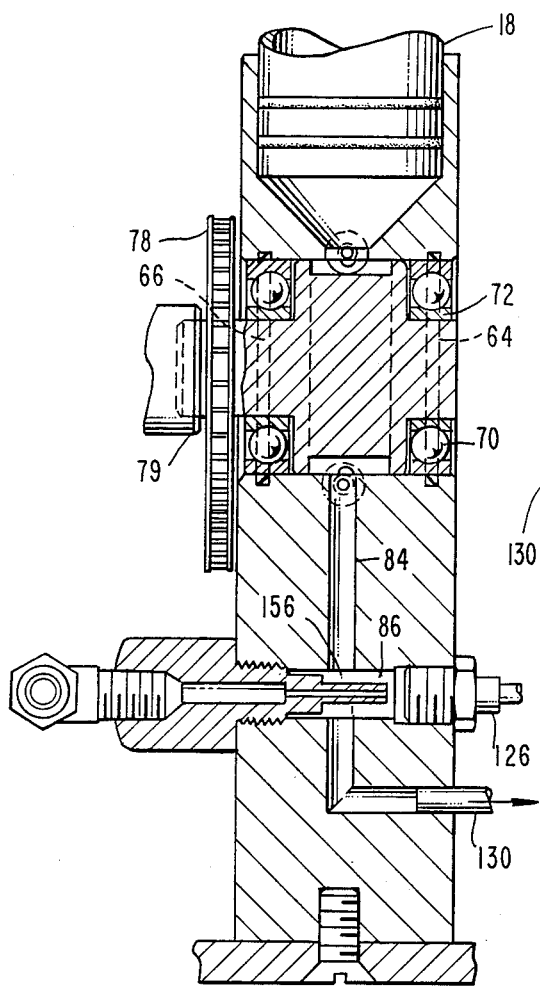
FIG. 5 is an exploded cross-sectional view of a portion of the solid particulate aerosol generator of FIG. 4 taken along plane 5—5.

The invention is a solid particulate aerosol generator and a method for using same.

With reference to the drawings, FIG. 1 is an external view of a solid particulate aerosol generator 10 embodying features of the invention. Shown in FIG. 1 is the aerosol generator external cabinet 12 which comprises a control panel 14 and a pair of attached foldable handles 16. Also shown in FIG. 1 is a particle reservoir 18 which protrudes through the top of the cabinet 12. Attached to the top of the particle reservoir 18 is an agitator motor housing 20.

Figure 6:
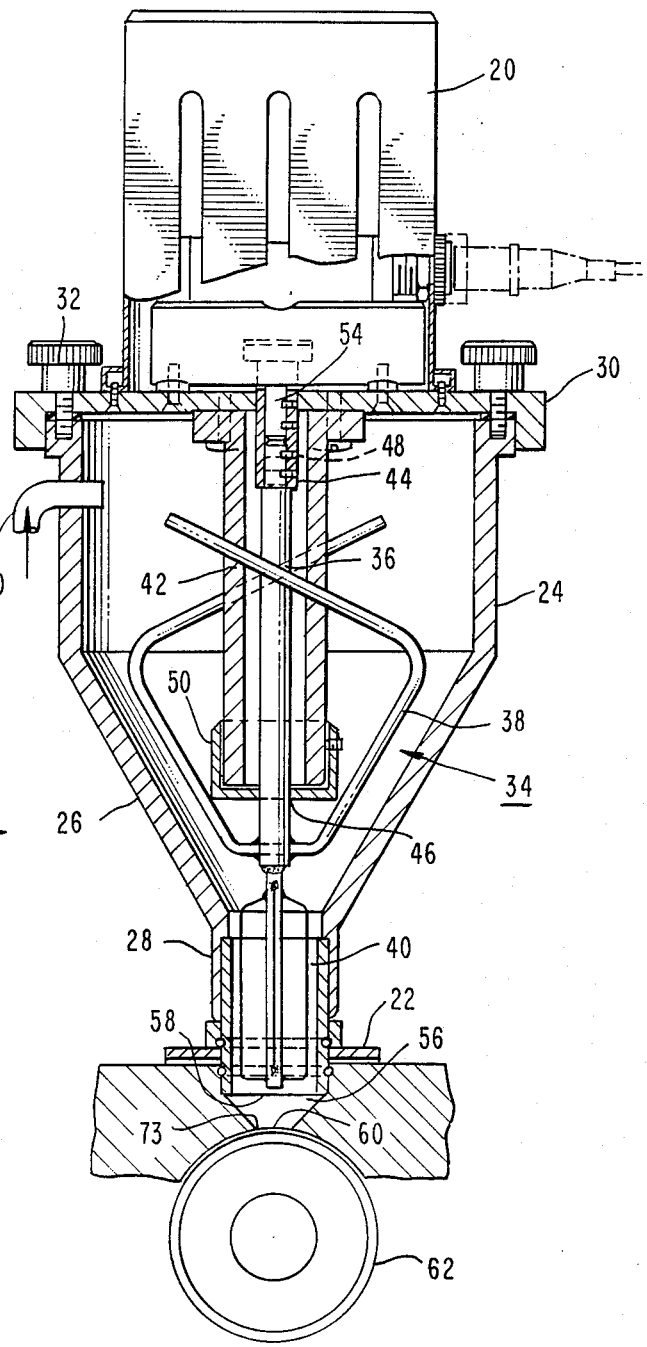
FIG. 6 is an exploded cross-sectional view of a solid particulate reservoir assembly useful in the embodiment of the solid particulate generator of the invention shown in FIG. 1.

As shown in FIGS. 1, 4 and 6, the particle reservoir 18 protrudes through the top wall 22 of the cabinet 12 where it is attached within the interior of the cabinet 12. The reservoir 18 comprises a reservoir hopper 24 in fluid communication with a reservoir conical section 26. The reservoir 18 further comprises a reservoir throat 28 in fluid communication with the reservoir conical section 26. The reservoir conical section 26 is disposed below the hopper 24 and is shaped like an inverted cone or pyramid. The hopper 24 is enclosed from above by a reservoir cover 30. The cover 30 is attached to the hopper 24 by a plurality of quick-change thumb screws 32.

A reservoir agitator 34 is disposed within the reservoir 18 and is adapted to prevent particulate material within the reservoir 18 from bridging. The agitator 34 comprises an agitator shaft 36, one or more reservoir hopper stirring arms 38 and reservoir throat stirring wires 40. The stirring arms 38 are adapted to protrude into the interior of the hopper 24 and the reservoir conical section 26 without touching the hopper or reservoir conical section walls, and to stir particulate matter within the hopper 24 and the reservoir conical section 26 when the agitator shaft 36 is rotated. The throat stirring wires 40 are adapted to protrude into the throat 28 without touching the walls of the throat 28 and to stir particulate matter within the throat 2 when rotated by the agitator shaft 36.

The agitator shaft 36 can be secured within the reservoir 18 by an agitator shaft housing 42 which is vertically disposed within the center of the hopper 26 and attached to the underside of the reservoir cover 30. The agitator shaft 36 is rotatably secured within the shaft housing 42 by an upper shaft bushing 44, by a lower shaft bushing 46 and by retaining rings 48. The upper shaft bushing 44 is disposed and attached within the upper end of the shaft housing 42. The lower shaft bushing 46 is disposed and attached within a shaft housing cover 50 which encloses the shaft housing 42 at its lower end. Alternatively, the agitator shaft 36 can be secured within the reservoir cover 30 by a sufficiently rigid upper shaft bushing 44 to dispense with the need for the agitator shaft housing 42, the shaft housing cover 50 and the lower shaft bushing 46.

The agitator shaft 36 is rotatably driven by an agitator motor (not shown) disposed within the agitator motor housing 20 which is attached on the upper side of the reservoir cover 30. The agitator motor turns an agitator motor drive shaft 54 which is vertically disposed to protrude through a centrally located opening in the reservoir cover 30 to engage the agitator shaft 36. The connection between the drive shaft 54 and the agitator shaft 36 can be accomplished with a set-screw connector. Alternatively, the connection can be of a "quick-release" type, so that the reservoir cover 30, including the agitator motor, can be quickly and easily removed from the hopper 26. Such quick-release connection can be magnetic or it can be a mechanical key-and-slot combination.

In one alternative design, the reservoir 18 and the agitator 34 are adapted for sale as a disposable unit. The reservoir 18 and the agitator 34 are adapted with "quick-change" attachment connections interfacing with the cabinet 20 and the agitator motor, respectively, and the reservoir 18 is sold pre-loaded with an appropriate powder.

As illustrated in FIGS. 4 and 5, the reservoir throat 28 is in fluid communication with a reservoir discharge chamber 56 disposed within and attached to the cabinet 12. The discharge chamber 56 can be a conduit. The discharge chamber 56 has an uper discharge chamber opening 58 which is in fluid communication with the reservoir throat 28. The discharge chamber 56 also comprises a lower discharge chamber opening 60. Preferably, the discharge chamber 56 is conical in shape, with the upper chamber opening 58 being larger in diameter than the lower chamber opening 60, so that the reservoir chamber 56 can accumulate particulate matter gravitating out of the lower end of the reservoir throat 28 and funnel such particulate matter through the smaller lower chamber opening 60.

A powder proportioning wheel 62 is rotatably disposed immediately below the lower discharge chamber opening 60, such that the axis of rotation 136 of the wheel 62 is horizontally disposed. The wheel 62 can be a right circular cylinder having a first end surface 138, a second end surface 140 and a continuous radial surface 142 (the surface parallel to the axis of rotation 136). The radial surface 142 abuts the first end surface 138 along a first radial edge 144 and the radial surface 142 abuts the second end surface 140 along a second radial edge 146. The radial surface 142 has an upper radial surface moiety 148 above the axis of rotation 136 and a lower surface moiety 150 below the axis of rotation 136. The wheel 62 can have a diameter between about 1 and about 1½ inches.

A first o-ring groove 64 is disposed radially around the radial surface 142 proximate to the first radial edge 144, and a second o-ring groove 66 is disposed around the radial surface 142 proximate to the second radial edge 146. The first o-ring groove 64 and the second o-ring groove 66 are disposed in parallel planes which are perpendicular to the axis of rotation 136.

A first o-ring 152 is disposed within the first o-ring groove 64, and a second o-ring 154 is disposed within the second o-ring groove 66.

A plurality of pockets 68 are disposed radially about the radial surface 142. The pockets 68 may be indentations in the radial surface 142. A typical wheel 62 can have about 24 pockets 68. The pockets 68 are spaced at equal distances radially about the wheel 62. The pockets 68 each comprise a predetermined pocket volume and a single open side. Preferably, the powder proportioning wheel 62 comprises at least four pockets 68, so that the delivery of powder by the rotating wheel 62 approximates continuous flow. In a typical wheel 62, the volume of each pocket 68 can be between about .004 and about .008 cubic inches.

The wheel 62 is rotatably attached to and disposed within the cabinet 12. Such attachment may be accomplished by supporting the wheel 62 on a plurality of ball bearings 70 rotatably disposed within ball bearing housings 72 which, in turn, are disposed within and attached to the cabinet 12. The wheel 62 is disposed in close proximity to the edge 73 of the lower chamber opening 60 so that the edge 73 can act as a scraping means to trim off powder disposed above the open side of the pocket 68 as the wheel 62 is rotated. To minimize the quantity of powder carried on the surface of the wheel 62 and outside of the pockets 68, the wheel 62 is preferably disposed within about 0.002 inches of the edge 73.

The wheel can be rotatably driven by direct linkage to an electric motor (not shown). A tacometer (not shown) housed within tacometer housing 74 can be used to monitor the rotation speed of the wheel 62. The wheel 62 can be linked to the tacometer via a chain 76. The chain 76 can rotatably link the wheel 62 and the tacometer via a wheel chain sprocket 78 which is rotatably attached to the wheel 62 orthogonal to the axis of rotation of the wheel 62 by means of a drive hub 79 and tacometer chain sprocket 82 which is rotatably attached to a tacometer drive shaft 80.

The speed at which the electric motor turns the wheel 62 can be controlled by any of several conventional electrical control devices such as a rheostat (not shown). By varying the speed of the electric motor, the speed of the powder proportioning wheel 62 can be varied over a wide range.

Disposed below the powder proportioning wheel 62 is a metered powder conveying conduit 84 adapted to accept powder falling by gravity out of the powder proportioning wheel pockets 68 and conveying the metered powder to a venturi mixer 86 (described below). The metered powder conveying conduit 84 is attached to the cabinet 12 and disposed below the pockets 68 on the powder proportioning wheel 62 at a location below the center-line of the powder proportioning wheel 62. Preferably, the metered powder conveying conduit 84 is disposed immediately below the lowermost of the pockets 68. The metered powder conveying conduit 84 is disposed in such a manner that as the powder proportionng wheel 62 rotates, powder within the pockets 68 gravitates out of the pockets 68 and into the metered powder conveying conduit 84.

The metered powder conveying conduit 84 is in fluid communication with the throat 156 of the venturi mixer 86. The metered powder conveying conduit 84 enters the throat 156 of the venturi mixer 86 orthagonal to the main flow of any fluid through the throat 156 (along the longitudinal axis) of the venturi mixer 86 such that when fluid is flowing through the throat 156 of the venturi mixer 86, particulate matter within the metered powder conveying conduit 84 is drawn by vacuum into the throat 156 of the venturi mixer 86 where it is mixed with the fluid flowing through the throat 156 to form a fluid-particulate mixture.

Alternatively, the invention can comprise electrical neutralizing equipment (not shown).

Alternatively, the reservoir 18 and the components disposed below the reservoir 18 (as shown in FIG. 5) can be housed in a separate compartment (not shown) to the rear of and outside of the cabinet 20. This alternative cabinet 20. This alternative configuration has the advantage of granting easy cleaning and maintenance access to the various powder handling components.

Figure 7:
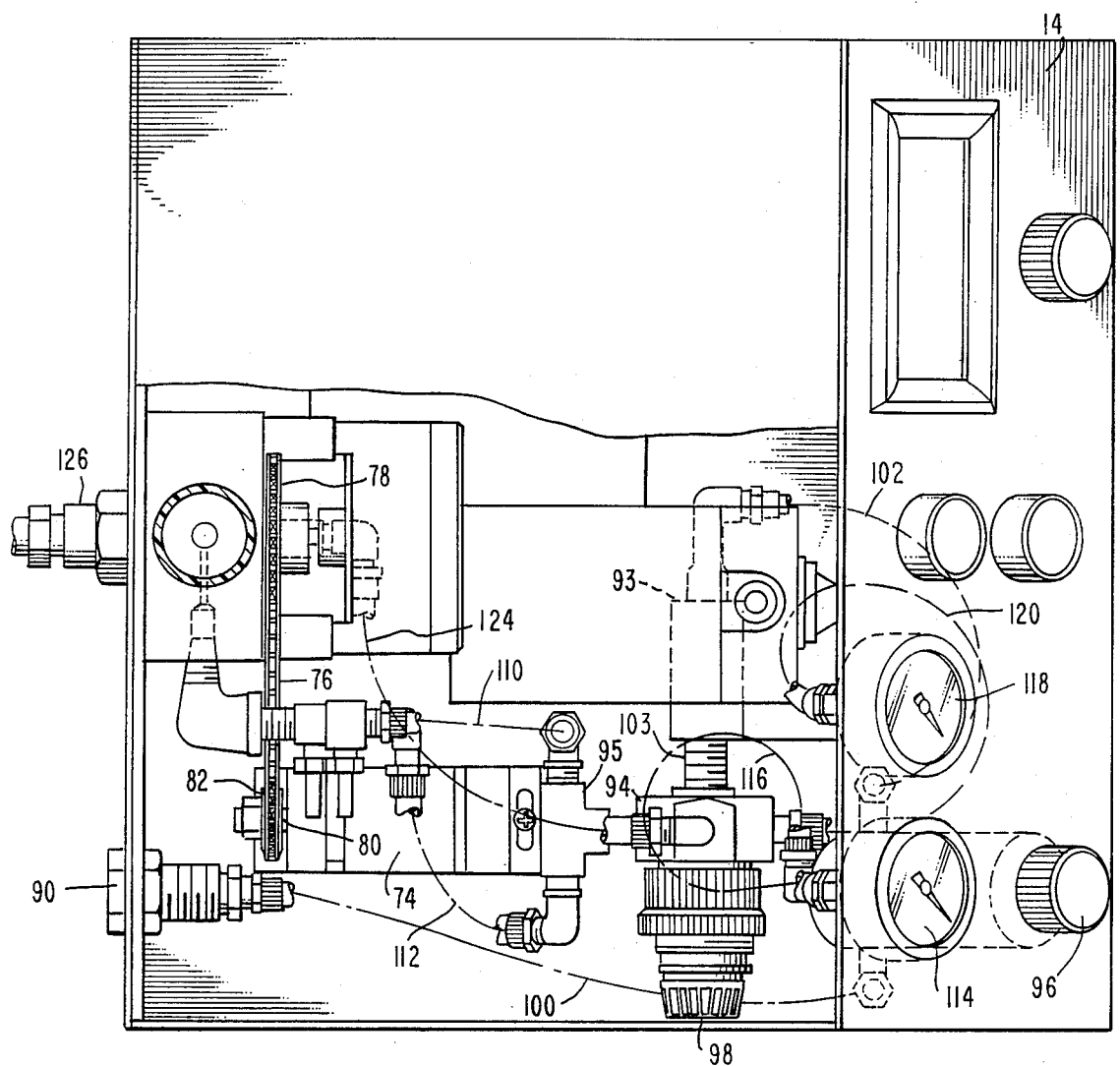
FIG. 7 is a partial cross-sectional view of the solid particulate aerosol generator of FIG. 1 taken along plane 7—7.
Figure 8:
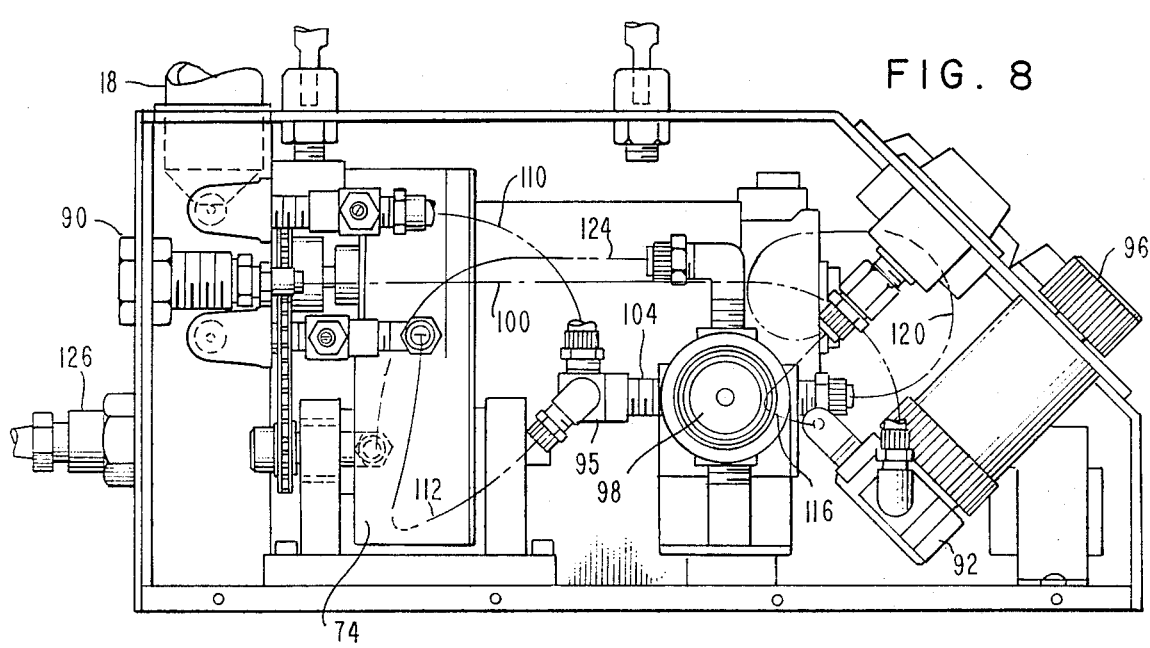
FIG. 8 is a cross-sectional view of the solid particulate aerosol generator of FIG. 1 taken along plane 8—8.

As shown in FIGS. 7 and 8, a carrier gas inlet port 90 which may comprise a piping or tubing connection is disposed within and attached to the rear wall of the cabinet 12. Also disposed within and attached to the cabinet 12 is a primary pressure regulator 92, a solenoid-activated valve 93, a secondary pressure regulator 94, and a needle valve 95. The primary pressure regulator 92 is preferably adjustable by a primary pressure regulator knob 96 located on the panel 14. The secondary pressure regulator 94 is preferably adjustable by a secondary pressure regulator knob 98 disposed within the cabinet 12.

The inlet port 90 is in fluid communication with the inlet side of the primary pressure regulator 92 via a carrier gas inlet conduit 100. The discharge side of the primary pressure regulator 92 is in fluid communication with the inlet side of the solenoid-actuated valve 93 via an intermediate carrier gas conduit 102. The discharge side of the solenoid-actuated valve 93 is in fluid communication with the inlet side of the secondary pressure regulator 94 via nipple 103. The discharge side of the secondary pressure regulator 94 is in fluid communicaton with the needle valve 95 via a secondary pressure regulator bleedstream discharge conduit 104. The needle valve 95 is in fluid communication with a reservoir gas injector 106 and a powder proportionng wheel discharge gas injector 108 via a reservoir injector gas conduit 110 and a powder proportioning wheel discharge gas injector conduit 112, respectively. The reservoir gas injector 106 is disposed within the cabinet 12 and adapted to direct a small stream of gas up into the reservoir discharge chamber 56 to upwardly aerate the discharge chamber 56 and the reservoir 18. The powder proportioning wheel discharge gas injector 108 is disposed within the cabinet 12 and adapted to direct a small stream of gas up into the lower-most pocket 68 on the powder proportioning wheel 62.

A primary carrier gas pressure gauge 114 is attached to the panel 14 an adapted to be in fluid communication with the carrier gas inlet conduit 100 via a primary pressure gauge conduit 116. A secondary carrier gas pressure gauge 118 is also attached to the panel 14 and is adapted to be in fluid communication with the secondary pressure regulator discharge conduit 104 via a secondary pressure gauge conduit 120.

The secondary pressure regulator 94 is in fluid communication with the inlet side of the venturi mixer 86 via a secondary pressure regulator main discharge conduit 124. The discharge side of the venturi mixer 86 is in fluid communication with a gas-solids delivery port 126 which is installed within the wall of the cabinet 12 and is preferably adapted with a piping or conduit fitting 128.

A reservoir vent conduit 130 is disposed in fluid communication with the reservoir hopper 24 at its one end and with the throat of the venturi mixer 86 at its other end. The vent conduit 130 is adapted to prevent the overpressuring of the reservoir 18 by gas injected into the reservoir by the reservoir gas injector 106.

In operation, particulate powder is stored within the reservoir 18. The powder within the reservoir 18 is prevented from bridging by agitation delivered by the reservoir agitator 34 as driven by the agitator motor via the agitator shaft 36. The powder gravitates from the reservoir 18 through the reservoir throat 28 and into the reservoir discharge chamber 56 via the upper chamber opening 58. A small stream of gas is upwardly injected into the reservoir throat 28 via the reservoir gas injector 106 to aerate the particulate matter within the reservoir throat 28 and to further prevent particulate bridging within the reservoir throat 28. Any overpressure of gas in the reservoir 18 is bled off to the venturi mixer 86 via the reservoir vent conduit 130.

The particulate matter within the reservoir discharge chamber 56 gravitates through the lower chamber opening 60 to the top of the powder proportioning wheel 62 and is deposited in the upper-most of the pockets 68.

The o-rings 152 and 154 disposed in the o-ring grooves 64 and 66 seal the sides of the wheel 62 to prevent powder from leaking over the radial edges 144 and 146 of the wheel 62. The powder proportioning wheel 62 is rotated by the electric motor. As the powder proportioning wheel 62 is rotated, excess powder above the surface of the powder proportioning wheel is scraped off by the edge 73 of the lower chamber opening 60. Thus, after the powder proportioning wheel 62 rotates a pocket 68 past the edge 73, the amount of powder within that pocket 68 is almost precisely the volume of the pocket 68.

With a typical wheel 62 of between about 1 and about 1-68 having a volume between about 0.004 and about 0.008 cubic inches, a typical rotation speed is between about 1 and about 21 rpm.

Each pocket 68 rotated past the edge 73 is further rotated to the lower-most part of the wheel 62, whereupon the powder falls by gravity out of the pocket 68 and into the metered powder conveying conduit 84. Gas from the powder proportioning wheel discharge gas injector 108 assists in this process by gently blowing powder out of the pocket 68.

In the metered powder conveying conduit 84, powder gravitates downwardly towards the venturi mixer 86. As will be described below, carrier gas is caused to flow through the venturi mixer 86 along the venturi's longitudinal axis, thereby creating a vacuum within the throat 156 of the venturi mixer 86. Such vacuum has the affect of drawing powder from the metered powder conveying conduit 84 into the throat 156 of the venturi mixer 86 and mixing such powder with the carrier gas. The gas-solids mixture is then discharged out of the venturi mixer 86 and out of the gas-solids discharge port 126 to a suitable conduit (not shown) whereby the gas-solids mixture is transported to the target location and allowed to flow out into the atmosphere as a solid particulate aerosol.

The solenoid switch is activated to open the solenoid-actuated valve 93. Moisture free carrier gas is brought into the cabinet 12 via the carrier gas inlet 90. The carrier gas can be any suitable gaseous material suitable for forming a solids-particulate aerosol. The gas can be air or it can be some inert material such as nitrogen. The gas is urged to flow into the inlet 90 via an externally-located propelling means such as a compressor or compressed gas cylinder (not shown). As the carrier gas flows through the carrier gas inlet 90 and passes into the carrier gas inlet conduit 100 it flows into the primary pressure regulator 92 wherein the gas pressure is reduced to a predetermined value by manipulating the primary pressure regulator knob 96 while reading the pressure on the primary pressure gauge 114.

The carrier gas flows out of the primary pressure regular 92 and into the secondary pressure regulator 94 via the intermediate carrier gas conduit 102, solenoid-actuated valve 93 and nipple 103. Within the secondary pressure regulator 94, the gas pressure is further reduced to a value which can be controlled by manipulating the secondary pressure regulator knob 98 while reading the pressure on the secondary pressure gauge 116.

Gas from the secondary pressure regulator 94 is then split into three streams. The primary stream flows to the venturi mixer 86 via the secondary pressure regulator main discharge conduit 124. As described above, this primary stream is mixed with powder from the metered powder conveying conduit 84 in the venturi mixer 86 to form a gas-solids mixture which is discharged from the cabinet 12 via the gas-solids discharge port 126.

A bleed-stream of gas from the secondary pressure regulator 94 flows through the needle valve 95 via the secondary pressure regulator bleed-stream discharge conduit 104. The bleed-stream has a substantially reduced pressure and flow rate by flowing through the needle valve 95. The bleed-stream is then split into two separate sub-streams. One of the sub-streams flows to the reservoir gas injector 106 via the reservoir gas injector conduit 110. The other sub-stream flows to the powder proportioning wheel discharge gas injector 108 via the powder proportioning wheel discharge gas injector conduit 112. As described above, the gas flowing through the reservoir gas injector 106 is used to aerate the powder material within the reservoir throat 28. Also as described above, the gas flowing through the powder proportioning wheel discharge gas injector 108 is used to gently blow powder material out of the pockets 68 and into the metered powder conveying conduit 84. In a typical operation, the flow rate of aerating gas flowing through the reservoir gas injector 106 and the powder proportioning wheel discharge gas injector 108 can be about 0.3 scfm.

The pressure of the carrier gas in the secondary pressure regulator main discharge conduit 124 can be controlled to any value which delivers a steady flow of the desired quantity of carrier gas to the venturi mixer 86. Preferably, the pressure in the secondary pressure regulator main discharge conduit 124 is maintained by reducing the pressure of the carrier gas in the carrier gas inlet conduit 100 in two steps. In the first step, the pressure of the carrier gas in the carrier gas inlet conduit 100 is reduced to between about 35 psig and about 45 psig by the primary pressure regulator 92. The carrier pressure downstream of the primary pressure regulator 92 is further reduced by the secondary pressure regulator 94 to between about 18 psig and about 25 psig. The set point on the primary pressure regulator 92 is adjustable by the primary pressure regulator control knob 96 (located on the panel 14) up to some maximum pressure, for instance 40 psig. The secondary pressure regulator 94, whose control knob 98 is disposed within the cabinet 12 and so is not normally accessible to the operator, is set to deliver a maximum pressure when the inlet pressure (from the primary pressure regulator 92) is relatively high (for instance, above 22 psig) and to go full open when the inlet pressure is low (e.g. below about 22 psig). By this two-step method, the pressure of the carrier gas to the venturi mixer 86 is controllable by manipulating the set point of the primary pressure regulator 92, while the secondary pressure regulator 94 acts to prevent over-pressuring at the venturi mixer 86 inlet.

Although the present invention has been described in considerable detail with reference to certain preferred versions, many other versions should be apparent to those skilled in the art. For example, the powder proportioning wheel 62 need not be a wheel at all. It could be any rotatable continuous surface having at least one indentation. Therefore the spirit and scope of the appended claims should not necessarily be limited to the description of the preferred versions contained herein.

What is claimed is:

1. A solid particulate aerosol generator for accurately dispersing a predetermined quantity of a solid particulate material having a mean diameter less than about 0.2 microns so as to provide a highly precise aerosol concentration of the particulate material which is useful in the testing of HEPA filters, the solid particulate aerosol generator comprising:

(a) a reservoir for storing the solid particulate material;

(b) a wheel rotatable about a horizontal axis of rotation, the wheel being disposed below and in fluid communication with the reservoir, the wheel being a right circular cylinder having a first end surface, a second end surface and a continuous radial surface, the radial surface abutting the first end surface along a first radial edge and the radial surface abutting the second end surface along a second radial edge, the radial surface having an upper radial surface moiety above the axis of rotation and a lower radial surface moiety below the axis of rotation;

(c) a first o-ring groove disposed radially around the radial surface proximate to the first radial edge and a second o-ring groove disposed radially around the radial surface proximate to the second radial edge, the first o-ring groove and the second o-ring groove being disposed in parallel planes which are perpendicular to the axis of rotation;

(d) a first o-ring disposed within the first o-ring groove and a second o-ring disposed within the second o-ring groove;

(e) at least four pockets disposed evenly around the radial surface between the o-ring grooves, each pocket having a predetermined volume and a single open side;

(f) scraping means disposed proximate to the radial surface upper moiety for scraping excess solid particulate material from above the single open side of each pocket;

(g) a conveying conduit disposed below and in fluid communication with the radial surface lower moiety; and (h) a venturi mixer having a throat in fluid communication with the conveying conduit and having an inlet side and a delivery port.

2. The solid particulate aerosol generator of claim 1 wherein the pockets are indentations defined within the radial surface of the wheel.

3. The solid particulate aerosol generator of claim 1 wherein the predetermined volume of each pocket is between about 0.004 and about 0.008 cubic inches.

4. The solid particulate aerosol generator of claim 1 wherein the reservoir is agitated.

5. The solid particulate aerosol generator of claim 1 wherein the reservoir comprises an agitator.

6. The solid particulate aerosol generator of claim 1 wherein the reservoir is aerated.

7. The solid particulate aerosol generator of claim 1 wherein the pockets on the radial surface lower moiety are aerated.

8. The solid particulate aerosol generator of claim 1 wherein the speed at which the wheel is rotatable is variable.

9. A method for producing a solid particulate aerosol comprised of particles having a mean diameter less than about 0.2 microns comprising the steps of:

(a) conveying solid particulate material from a reservoir to a rotating wheel wherein the wheel is rotatable about a horizontal axis of rotation, the wheel being disposed below and in fluid communication with the reservoir, the wheel being a right circular cylinder having:

(i) a first end surface, a second end surface and a continuous radial surface, the radial surface abutting the first end surface along a first radial edge and the radial surface abutting the second end surface along a second radial edge, the radial surface having an upper radial surface moiety above the axis of rotation and a lower radial surface moiety below the axis of rotation;

(ii) a first o-ring groove disposed radially around the radial surface proximate to the first radial edge and a second o-ring groove disposed radially around the radial surface proximate to the second radial edge, the first o-ring groove and the second o-ring groove being disposed in parallel planes which are perpendicular to the axis of rotation;

(iii) a first o-ring disposed within the fist o-ring groove and a second o-ring disposed within the second o-ring groove;

(iv) at least four pockets disposed evenly around the radial surface between the o-ring grooves, each pocket having a predetermined volume and a single open side; the solid particulate material being conveyed to the wheel so that the solid particulate material is deposited into the pockets at a first location on the upper radial surface moiety;

(b) rotating the wheel to convey the pockets containing the solid particulate material from the first location to a second location on the lower radial surface moiety;

(c) conveying the solid particulate material from the pockets at the second pocket location to a conduit wherein is flowing a gas;

(d) distributing the solid particulate material into the flowing gas to form a gas-solid mixture; and (e) discharging the gas-solid mixture into the atmosphere.

10. A method for testing a HEPA filter comprising the steps of:

(a) exposing the HEPA filter to a solid particulate aerosol produced by the method defined in claim 9; and (b) measuring the quantity of particles passing through the HEPA filter from the solid particulate aerosol to the atmosphere on the opposite side of the HEPA filter.

11. The method of claim 9 wherein the solid particulate material is conveyed from the reservoir in step(a) by gravity.

* * * * *